(12) United States Patent
Gossler et al.

(10) Patent No.: US 10,276,631 B2
(45) Date of Patent: Apr. 30, 2019

(54) METHOD FOR PRODUCING A MICRO-LED MATRIX, MICRO-LED MATRIX AND USE OF A MICRO-LED MATRIX

(71) Applicants: Fraunhofer-Gesellschaft zur Forderung der angewandten Forschung e.V., Munich (DE); Albert-Ludwigs-Universitat Freiburg

(72) Inventors: Christian Gossler, Freiburg (DE); Ulrich Schwarz, Freiburg (DE); Patrick Ruther, Karlsruhe (DE)

(73) Assignees: Fraunhofer-Gesellschaft zur Förderung der angewandten Forschung e.V., Munich (DE); Albert-Ludwigs-Universität Freiburg, Freiburg (DE)

( * ) Notice: Subject to any disclaimer, the term of this patent is extended or adjusted under 35 U.S.C. 154(b) by 980 days.

(21) Appl. No.: 14/042,991

(22) Filed: Oct. 1, 2013

(65) Prior Publication Data
US 2014/0094878 A1 Apr. 3, 2014

(30) Foreign Application Priority Data
Oct. 1, 2012 (DE) .................. 10 2012 217 957

(51) Int. Cl.
*H01L 33/00* (2010.01)
*H01L 29/18* (2006.01)
(Continued)

(52) U.S. Cl.
CPC .......... *H01L 27/156* (2013.01); *A61N 5/0601* (2013.01); *A61N 5/0622* (2013.01);
(Continued)

(58) Field of Classification Search
CPC ................ H01L 27/156; H01L 27/153; H01L 27/11565; H01L 33/08; A61N 2005/0652
See application file for complete search history.

(56) References Cited

U.S. PATENT DOCUMENTS

| 6,613,610 B2* | 9/2003 | Iwafuchi | H01L 21/2007 257/E21.122 |
| 7,202,141 B2* | 4/2007 | Park | B23K 26/0732 257/E21.347 |

(Continued)

FOREIGN PATENT DOCUMENTS

WO 2010132552 11/2010

OTHER PUBLICATIONS

Koo, M. et al., "Biointegrated Flexible Inorganic Light Emitting Diodes", Nanobiosensors in Disease Diagnosis, Dovepress, pp. 5-15, Mar. 14, 2012.

(Continued)

*Primary Examiner* — Jesse Y Miyoshi
(74) *Attorney, Agent, or Firm* — Volpe and Koeing, P.C.

(57) ABSTRACT

A method for producing a micro-LED matrix by (A) depositing an LED layer structure onto a working substrate; (B) singulating a plurality of LED structures from the LED layer structure on the working substrate; (C) applying a first contact-making structure to a carrier substrate; and (D) transferring the plurality of LED structures from the working substrate to the carrier substrate by bonding and laser lift-off. An at least two-layered carrier substrate is used, including a carrier layer and a first flexible polymer layer, in step C the first contact-making structure is applied indirectly or directly to a side of the first polymer layer which faces away from the carrier layer, and in an additional method step D-0 between method steps C and D, a second flexible (Continued)

polymer layer is formed at least between the singulated LED structures. A micro-LED matrix and use are also provided.

7 Claims, 5 Drawing Sheets

(51) Int. Cl.
    *H01L 27/15*     (2006.01)
    *H01L 25/075*     (2006.01)
    *H01L 33/62*     (2010.01)
    *A61N 5/06*     (2006.01)
    *H01L 33/08*     (2010.01)
    *H01L 33/32*     (2010.01)
    *A61N 1/05*     (2006.01)

(52) U.S. Cl.
    CPC ...... *H01L 25/0753* (2013.01); *H01L 33/0079* (2013.01); *H01L 33/08* (2013.01); *H01L 33/62* (2013.01); *A61N 1/0541* (2013.01); *A61N 1/0551* (2013.01); *A61N 2005/0652* (2013.01); *H01L 33/32* (2013.01)

(56) References Cited

U.S. PATENT DOCUMENTS

| | | | |
|---|---|---|---|
| 8,933,433 B2* | 1/2015 | Higginson | H01L 23/3171 257/13 |
| 9,029,880 B2* | 5/2015 | Sakariya | H01L 27/124 257/88 |
| 9,299,887 B2* | 3/2016 | Lowenthal | H01L 33/08 |
| 2010/0317132 A1* | 12/2010 | Rogers | H01L 25/0753 438/27 |
| 2011/0215365 A1 | 9/2011 | Lin | |

OTHER PUBLICATIONS

Day, J. et al., "Full-Scale Self-Emissive Blue and Green Microdisplays Base don GaN Micro-LED Arrays", Proc. SPIE 8268, 82681 (2009).

* cited by examiner

METHOD FOR PRODUCING A MICRO-LED MATRIX, MICRO-LED MATRIX AND USE OF A MICRO-LED MATRIX

INCORPORATION BY REFERENCE

The following documents are incorporated herein by reference as if fully set forth: German Patent Application No. 102012217957.7, filed Oct. 1, 2012.

BACKGROUND

The invention relates to a method for producing a micro-LED matrix, and to a micro-LED matrix, and to a use of such a micro-LED matrix.

For producing micro-LED matrices it is known to produce LED structures on a first substrate and subsequently to transfer them to a second substrate via a bonding and laser lift-off process.

By way of example, J. Day et al., *Full-Scale Self-Emissive Blue and Green Microdisplays Based on GaN Micro-LED Array*, Proc. SPIE 8268, 82681 (2009), describe a method in which GaN-based matrices of micro-LEDs are produced on fixed substrates and fabricated by a bonding process. The individual micro-LEDs are provided with CMOS circuits for individual driving.

What is disadvantageous about the methods according to the prior art is that the components based on the micro-LED matrices produced are not flexible and have lateral dimensions and thicknesses greater than 100 μm. Although these rigid components can be used in the field of biophysics, the possibilities for use are greatly restricted on account of the dimensions and inflexibility of said components.

SUMMARY

Therefore, the present invention is based on the object of providing a method for producing micro-LED matrices which makes it possible to produce micro-LED matrices which are embedded into a flexible layer and which are simultaneously biocompatible and thus usable in the human organism and have the smallest possible dimensions. Furthermore, the invention is intended to provide such a micro-LED matrix.

This object is achieved by a method and by a micro-LED matrix including one or more features of the invention. Advantageous configurations of the method and of the micro-LED matrix are found below and in the claims. In addition, this object is achieved by the use of a micro-LED matrix according to the invention.

The method according to the invention for producing a micro-LED matrix comprises the following method steps:

In a method step A an LED layer structure is deposited onto a working substrate.

In a method step B a plurality of LED structures are singulated from the LED layer structure on the working substrate.

In a method step C a first contact-making structure is applied to a carrier substrate.

In a method step D the plurality of LED structures are transferred from the working substrate to the carrier substrate by a bonding and laser lift-off process.

It is essential that an at least two-layered carrier substrate is used, which carrier substrate comprises a carrier layer and a first flexible polymer layer, in method step C the first contact-making structure being applied indirectly or preferably directly to that side of the first polymer layer which faces away from the carrier layer. It is furthermore essential that in an additional method step D-0 between method steps C and D a second flexible polymer layer is formed at least between the singulated LED structures.

The invention is based on the applicant's insight that through the use of a carrier substrate comprising a flexible polymer layer and the formation of a second flexible polymer layer between the singulated LED structures, the singulated LED structures can be embedded into a flexible environment. In this case, it lies within the scope of the invention that individual elements of the LED structures, in particular metallic contact structures, are formed after the embedding.

The method according to the invention thus affords for the first time a practicable possibility for producing micro-LED matrices, in particular GaN-based micro-LED matrices, on a flexible substrate. In comparison with previously known micro-LED matrices, which hitherto could only be produced on fixed substrates, the micro-LED matrices on a flexible substrate are suitable for use in the human organism. Furthermore, the method according to the invention makes it possible to produce micro-LED matrices on a flexible substrate which have individually drivable LED structures. In contrast to previously known methods, which combine already processed LEDs with a flexible matrix, with the method according to the invention very much smaller, thinner and more flexible micro-LED matrices can be produced by the transfer of the plurality of LED structures by the bonding and laser lift-off process.

The embedding of the LED structures into the second flexible polymer layer affords a further advantage: the semiconductor layers of the LED structures typically have horizontally an overhang relative to the first contact-making structure. This region is very sensitive and susceptible to breaking during the laser lift-off process on account of the brittle semiconductor material. There is the risk here of the LED structure breaking upon the action of force. As a result of the formation of the second flexible polymer layer in the local regions between the LED structures, flexible material is thus introduced between carrier substrate and working substrate; a so-called underfill process is therefore carried out. By the use of the underfill process, the overhang is embedded into the second flexible polymer layer. Consequently, the overhang is supported and acquires the necessary stability in particular for the laser lift-off process, without restricting the flexibility of the component.

In one preferred embodiment, in an additional method step E after method step D a third flexible polymer layer is applied to the second polymer layer and the embedded LED structures. This affords the advantage that an electrical insulation arises as a result of the third polymer layer, said electrical insulation likewise being flexible.

Advantageously, in an additional method step E-0 before method step E a second contact-making structure, preferably a metallic second contact-making structure, is applied at least to the embedded LED structures. This enables contact to be made with the LED structures in a simple manner by the first and second contact-making structures arranged on opposite sides. In particular, it is advantageous here for the second contact-making structure to be formed lithographically.

In a further advantageous embodiment, contact trenches to the second contact-making structure, which was applied in method step E-0, are opened in local regions of the third polymer layer. This advantageously takes place by dry etching via lithographically patterned resist masks. In addition, in local regions which do not coincide with the regions of the singulated LED structures and do not coincide with the regions of the contact trenches to the second contact-making structure, contact trenches to the first contact-making structure are opened on a side of the LED structure which faces the carrier substrate. The contact trenches to the first contact-making structure likewise extend through the second flexible polymer layer in addition to the third flexible polymer layer. This enables electrical contact to be made with the first and second contact-making structures in a simple manner through the respective contact trench.

However, it likewise lies within the scope of the invention for contact to be made with the first and second contact-making structures on the same side of the LED structure, in particular on that side of the LED structure which faces the carrier substrate.

In a further preferred embodiment, the plurality of LED structures are singulated in method step B by laser ablation and/or by a dry-chemical etching method. The process of laser ablation is preferably effected in accordance with R. Moser et al., "Laser processing of GaN-based LEDs with ultraviolet picosecond laser pulses", Proc. of SPIE, 8433, 84330Q1 2012. A dry-chemical etching method is described for example in Choi et al., "Fabrication of matrix-addressable micro-LED arrays based on a novel etch technique", Journal of Crystal Growth 268, 527 2004. At least the electrically active semiconductor layers of the LED layer structure between the LED structures are thereby removed. In method step B, therefore, spatial gaps arise between the singulated LED structures. These regions are configured in such a way that between the singulated LED structures there is at least no longer any mechanical and/or electronic connection through the semiconductor material. In this advantageous embodiment, therefore, method step B involves at least partly removing the LED layer structure between the LED structures, such that in addition to the electrical singulation a mechanical decoupling is obtained at least with regard to the semiconductor layers.

Advantageously, the semiconductor material is severed down to the plane of the working substrate; until method step D-0 is carried out, therefore, the LED structures are connected to one another only via the working substrate and possibly contact-making structures. What is advantageous here is that the singulation of the LED structures increases the flexibility of the component since there is no longer any rigid mechanical connection between the LED structures after method step B has been carried out: the fragile semiconductor material is removed in all regions with the exception of the LED structures, such that in the completed micro-LED matrix the individual LED structures are embedded in the flexible polymer layers movably with respect to one another.

In a further preferred embodiment, the second polymer layer is introduced into the region between the singulated LED structures in method step D-0 by the application of reduced pressure. In the context of this description, this means that the polymer used is sucked by reduced pressure into the region between the singulated LED structures. Preferably, this region is delimited by the singulated LED structures, the first polymer layer, the contact-making structure and the working substrate. The abovementioned underfill process therefore takes place. The singulated LED structures are stabilized by the second polymer layer, but the flexibility of the micro-LED matrix is maintained. Preferably, said underfill process takes place in such a way that the carrier substrate and the working substrate are arranged during this method step in such a way that the singulated LED structures on the working substrate are connected to a corresponding contact-making structure on the carrier substrate. This processing is called aligned wafer bonding. What is advantageous here is that the necessary stability whilst at the same time maintaining the flexibility of the component is achieved in a simple manner by the filling of the regions between the singulated LED structures with a flexible polymer.

In one preferred embodiment, the laser lift-off process in method step D takes place in at least two substeps: firstly, laser radiation is applied only in the local regions of the LED structures. In this case, laser radiation is applied preferably from the side of the working substrate through the working substrate. In this first substep, the LED structures are at least partly detached from the working substrate.

In a second substep, over the whole area that surface of the LED structures and of the second flexible polymer layer which adjoins the working substrate has laser radiation applied to it and is thereby detached from the working substrate. Preferably, the second application of laser radiation over the whole area takes place with a lower intensity, preferably approximately half the intensity of the first application in the local regions. The two-stage configuration of the application of laser radiation with two different intensity levels makes it possible to separate the working substrate from the surface of the LED structures and of the second flexible polymer layer, without damaging the polymer layer. The second flexible polymer layer could be damaged in the event of whole-area application of laser light having the higher intensity level. By use of this two-stage process, which results in whole-area application of laser radiation to the surface adjoining the working substrate, adhering material of the second flexible polymer layer and the LED structures is completely detached from the working substrate, which improves the quality of the laser lift-off process.

The LED layer structure according to the invention can be formed as a micro-LED layer structure in a manner known per se and is preferably formed in the manner comprising at least one p-doped layer and one n-doped layer. The p-doped layer and the n-doped layer are arranged indirectly or preferably directly successively. The p-doped layer and the n-doped layer are preferably formed as doped GaN layers. The use of further semiconductor materials for forming the LED layer structure likewise lies within the scope of the invention, in particular indium gallium aluminum phosphide (InGaAlP), which is preferably used for LEDs in the orange-red spectral range.

In a further preferred embodiment, the aligned wafer bonding, i.e. the connection of the singulated LED structures on the working substrate to the first contact-making structure on the carrier substrate, takes place by liquid phase diffusion bonding, preferably by the use of indium bonding metals and/or eutectic gold-tin bonding metals.

In a further preferred embodiment, a flexible biocompatible polymer, preferably polyimide, is used for at least one polymer layer. This makes possible use in the human organism. In particular, it is advantageous to form the outer layers of the micro-LED matrix from a biocompatible polymer, in particular polyimide. In the preferred configuration with three polymer layers, therefore, preferably at least the first and third flexible polymer layers are formed from biocompatible polymer, in particular polyimide. It likewise lies within the scope of the invention, for the purpose of increasing safety, to form all the flexible polymer layers from biocompatible polymer, in particular polyimide.

In the context of this description, "flexible" means that the modulus of elasticity of the flexible polymer and that of the material for the working and/or carrier substrate differ by a plurality of orders of magnitude, preferably by at least two, with further preference at least four, orders of magnitude, in particular by a factor in the range of 10 to 100, preferably 15 to 60.

Preferably, the modulus of elasticity of the flexible polymer lies in the range of 5000 MPa to 10 000 MPa, in particular 7000 MPa to 9000 MPa, preferably approximately 8830 MPa.

The polymer of at least the first polymer layer is advantageously chosen in such a way that the highest possible processing temperatures are permissible, preferably up to a temperature of 200° C., in particular preferably up to a temperature of 350° C. This temperature range is advantageous in order that the polymer withstands the process of aligned wafer bonding. By way of example, the polymers bisbenzocyclobutene (BCB), polyimide or polymethyl methacrylate (PMMA) fulfill the above-mentioned condition with regard to the temperature stability.

The process of aligned wafer bonding is advantageously designed in such a way that the first polymer layer is not heated above 400° C., preferably not heated above 200° C. In principle, bonding processes known per se can be employed. The bonding process is advantageously carried out at a minimum possible temperature.

In a further preferred embodiment, the carrier layer of the at least two-layered carrier substrate is removed by a peel-off process in a method step F. The rigid layer is thereby omitted, and so the micro-LED matrix no longer has any laterally continuous regions having high stiffness. The micro-LED matrix therefore contains only flexible substrate layers.

The object described above is furthermore achieved by a micro-LED matrix having one or more features of the invention. The micro-LED matrix according to the invention is preferably produced by the above-described method according to the invention or preferably a preferred embodiment of the method according to the invention. The method according to the invention is preferably designed for forming a micro-LED matrix according to the invention or a preferred embodiment thereof.

The micro-LED matrix according to the invention comprises a first contact-making structure and at least two LED structures, which LED structures are arranged in a common horizontal plane. It is essential that the micro-LED matrix comprises a first flexible polymer layer, on which polymer layer the LED structures are arranged indirectly or directly. In this case, the first contact-making structure is applied indirectly or directly on that side of the first polymer layer which faces the LED structures. It is furthermore essential that at least the region between the LED structures is filled with a second flexible polymer layer. This affords the abovementioned advantages with regard to the flexibility of the matrix.

In one preferred embodiment, a rigid carrier layer is arranged indirectly or preferably directly on that side of the first flexible polymer layer which faces away from the LED structure. In this advantageous embodiment, therefore, the carrier substrate is formed with at least two layers and comprises the rigid carrier layer, which is preferably formed from silicon, and the first flexible polymer layer. Functionally, therefore, the first flexible polymer layer is part of the micro-LED matrix. The rigid carrier layer serves in particular for producing and/or for transporting one or a plurality of micro-LED matrices arranged alongside one another on the carrier layer with a common carrier layer. The user can remove a micro-LED matrix for application by simply pulling it off the carrier layer.

In the context of this description, "rigid" means that the stiffness of the carrier layer is high relative to the stiffness of the first flexible polymer layer. Preferably, the modulus of elasticity of the carrier layer is lower than the modulus of elasticity of the first flexible polymer layer by a factor of at least 5, with further preference at least 10, in particular by a factor in the range of 15 to 60.

In a further preferred embodiment, the micro-LED matrix comprises a luminescence conversion element, in particular a luminescence conversion element which is active in a wavelength range greater than 530 nm. What is advantageous here is that through the use of the luminescence conversion element, the wavelength range in which the micro-LED matrix emits can be shifted into the range of longer wavelengths.

In a further preferred embodiment, the individual LED structures of the micro-LED matrix are individually drivable. The interconnection is preferably effected in such a way that the LED structures are connected to a number of lines electrically insulated from one another, each line making electrical contact with a plurality of LED structures and a combination of two lines making contact with exactly one LED, preferably each combination of two lines making contact with exactly one LED. With particular preference, the interconnection of the LED structures is effected according to a first scheme for the interconnection of the p-type contacts, and the interconnection of the n-type contacts is effected according to a second scheme, which differs from the first.

Advantageously, the interconnection of the p-type contacts according to the first scheme is effected in such a way that a number k of p-type leads are present. The LED structures are divided into k pairwise disjoint p-type subgroups and each lead makes contact with all p-type contacts of the p-type subgroup assigned to this lead.

Furthermore, the interconnection of the n-type contacts according to the second scheme is advantageously effected in such a way that a number m of n-type leads are present. The LED structures are divided into m pairwise disjoint n-type subgroups and each n-type lead makes contact with all n-type contacts of the n-type subgroup assigned to this n-type lead.

Preferably, each n-type subgroup contains maximally, preferably exactly, k LED structures. Likewise, each p-type subgroup contains maximally, preferably exactly, m LED structures.

What is essential to this advantageous configuration is that any arbitrary pair of an n-type and a p-type subgroup has maximally one, preferably exactly one, common LED structure. As a result, an arbitrary LED structure can be driven separately by the electrical driving of the n-type and p-type lines of those subgroups which comprise this LED structure. In this advantageous configuration, therefore, an arbitrary LED structure can be driven without the use of a CMOS structure merely by the choice of the suitable pair of n-type and p-type lines.

This type of contact-making enables a total of $x^2/2$ LED structures to be driven individually with a number of x p-type or n-type leads.

In a further preferred embodiment, the contact is made with the LED structures both on the front side and on the back side, with particular preference in such a way that during use each LED structure has a substantially vertical current flow. What is advantageous here is that the vertical current flow prevents the situation where the relatively large horizontal dimensions in comparison with the vertical dimensions lead to a high horizontal series resistance. By contrast, the small vertical dimensions of the LED structure lead only to a lower vertical series resistance.

In the context of this description, "contact is made on the front side and on the back side" means that the p-type and n-type contacts lie on mutually opposite sides of the electrically active layer structure.

Furthermore, it is possible to process a plurality of different layers of n-side contact metal one above another, in each case separated by an insulating layer, such as e.g. bisbenzocyclobutene (BCB) or polyimide. As a result, it is possible to reduce the lateral dimensions of the component, in particular, which are substantially limited by the number of metal strips lying alongside one another.

In a further preferred embodiment, the micro-LED matrix has a total thickness of less than 20 μm. With particular preference, this total thickness is achieved by the use of the first, second and third flexible polymer layers, the flexible polymer layers each having a thickness of approximately 5 μm. In comparison with conventional methods, which have very much greater total thicknesses just through the use of rigid substrates, such as, for example, sapphire having a thickness of at least 100 μm, here it is therefore possible to produce micro-LED matrices having a total thickness of a significantly smaller order of magnitude. This primarily improves the possibilities for use in biophysical applications, in particular implant-based applications, preferably in the human organism.

In a further preferred embodiment, the micro-LED matrix additionally comprises electrodes for electrically stimulating biological tissue and/or for measuring electrical potentials. As a result, the optical stimulation can be combined with electrical stimulation in one component.

In a further preferred embodiment, the micro-LED matrix is designed for stimulating genetically photosensitive nerve cells and/or for activating dyes and/or proteins. Local excitation with short-wave light is thereby possible, in particular in medical technology and biotechnology.

A further aspect of the invention relates to the use of a micro-LED matrix according to the invention or an advantageous embodiment for optically and/or electrically stimulating nerve cells, in particular for the use of cochlea implants. As a result, the advantage of optical excitation can be combined with the advantage of the flexible configuration of the micro-LED matrix.

The micro-LED matrix according to the invention can comprise a multiplicity of LED structures formed as micro-LED. For applications in medicine and biotechnology it is advantageous if the LED structures of the micro-LED matrix are arranged in a series.

The deposition of the LED structure onto the working substrate can take place in a manner known per se, in particular by metal organic vapor phase epitaxy (MOVPE), see H. Amano et al., "Metalorganic vapor phase epitaxial growth of a high quality GaN film using an AlN buffer layer", Appl. Phys. Lett. 48, 3 (1986), or less commonly by molecular beam epitaxy, see Grandjean et al., "Group-III nitride quantum heterostructures grown by molecular beam epitaxy", J. Phys.: Condens. Matter 13, 6945 (2001).

BRIEF DESCRIPTION OF THE DRAWINGS

Further advantageous features and embodiments of the present invention are explained below on the basis of exemplary embodiments and the figures. In this case, FIGS. 1 to 4 show schematic partial sectional diagrams of an exemplary embodiment of the method according to the invention for producing an exemplary embodiment of the micro-LED matrix according to the invention:

FIG. 1 shows a schematic illustration of a carrier substrate with an applied first contact-making structure;

FIG. 2 shows a schematic illustration of a working substrate after singulation of LED structures;

FIG. 3 shows a schematic illustration of the exemplary embodiment after the LED structures have been transferred to the carrier substrate;

FIG. 4 shows a schematic illustration of the exemplary embodiment after removal from a carrier layer of the carrier substrate;

DETAILED DESCRIPTION OF THE PREFERRED EMBODIMENTS

Figure 1:
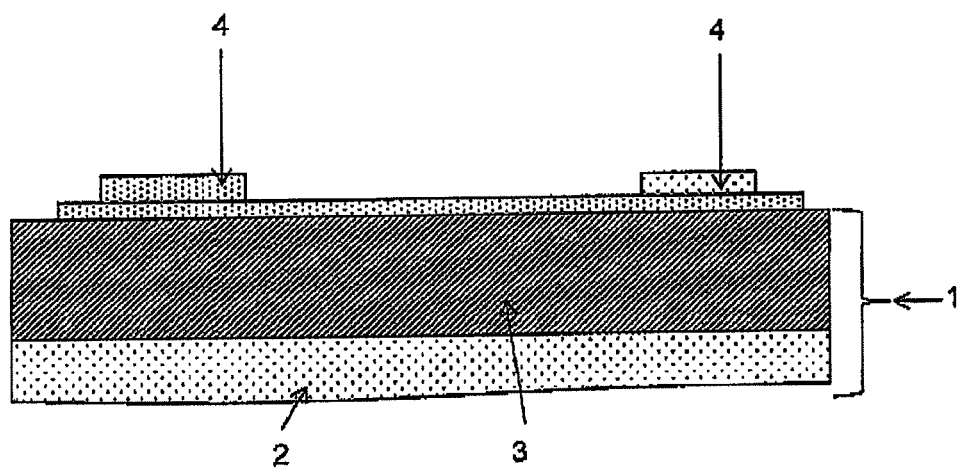

FIG. 1 shows the carrier substrate 1 with the first contact-making structure 4. The carrier substrate 1 consists of the carrier layer 2 and a first flexible polymer layer 3. The carrier layer 2 is a silicon layer, which, by virtue of its high stiffness, enables simple processing of the micro-LED matrix. The first flexible polymer layer 3 is applied to the carrier layer 2. Said first flexible polymer layer consists of a flexible biocompatible polymer having a modulus of elasticity of approximately 8830 MPa, for example polyimide. The thickness of the first flexible polymer layer 3 is approximately 5 μm.

FIG. 2 shows the working substrate 5 with a singulated LED structure 6 and a multilayered contact 9. The working substrate 5 is formed of sapphire, for example, and has a high stiffness. The dimensions of the singulated LED layer structure 6 are for example between 10 and 100 μm horizontally and approximately 5 μm vertically.

The LED structure 6 comprises an n-doped GaN layer 7 and a p-doped GaN layer 8. The multilayered contact 9 is applied to the p-type GaN layer 8. A lateral passivation layer 10a and 10b is additionally illustrated in FIG. 2. The passivation layers 10a and 10b are formed as silicon nitride or silicon oxide layers, in the present example illustrated in FIG. 1 as silicon nitride layer, and are applied by a PECVD method (plasma enhanced chemical vapor deposition) or sputtering method. As a result of the passivation layers 10a and 10b being applied, the individual LED structures 6 are electrically passivated and leakage currents and short circuits are avoided.

FIG. 2 thus shows the production process after the conclusion of a method step A, in which an LED layer structure is deposited onto the working substrate, and a method step B, in which a plurality of LED structures (only one LED structure is illustrated in FIG. 2) are singulated from the LED layer structure, for example by laser ablation. In addition, the lateral passivation layer was subsequently applied.

FIG. 1 correspondingly shows the production process after the conclusion of a method step C, in which the first contact-making structure is applied to the carrier substrate, in the present case to the first polymer layer of the carrier substrate.

Figure 2A:
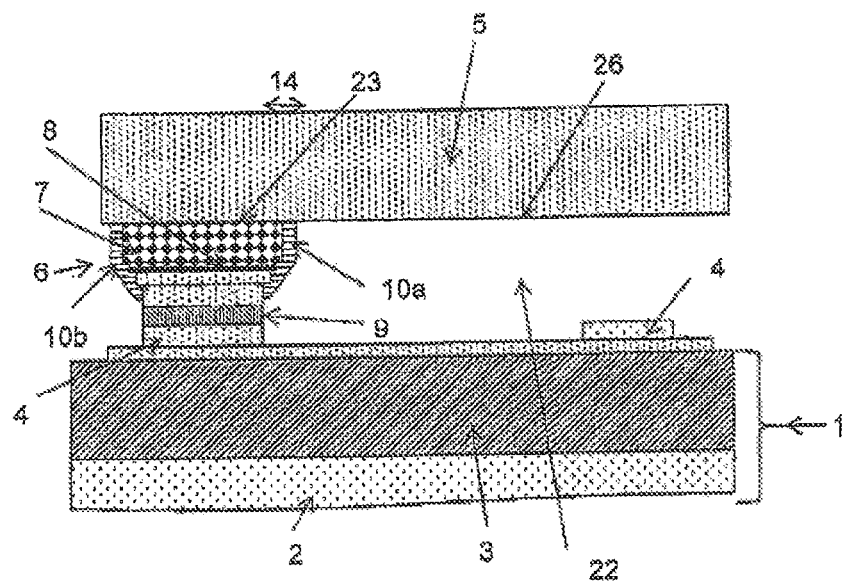
FIG. 2a shows a schematic illustration of the carrier substrate with attached working substrate after aligned wafer bonding.

During aligned wafer bonding, the carrier substrate 1 and the working substrate 5 are placed onto one another in such a way that the LED structure 6 is situated on that side of the working substrate 5 which faces the carrier substrate 1 and the first flexible polymer layer 3 is situated on that side of the carrier substrate 1 which faces the working substrate 5. The first contact-making structure 4 and the contact 9 are locally in contact with one another. The carrier layer 2 is therefore situated on that side of the first flexible polymer layer 3 which faces away from the LED structure 6. This state is illustrated in FIG. 2*a*.

Figure 2B:
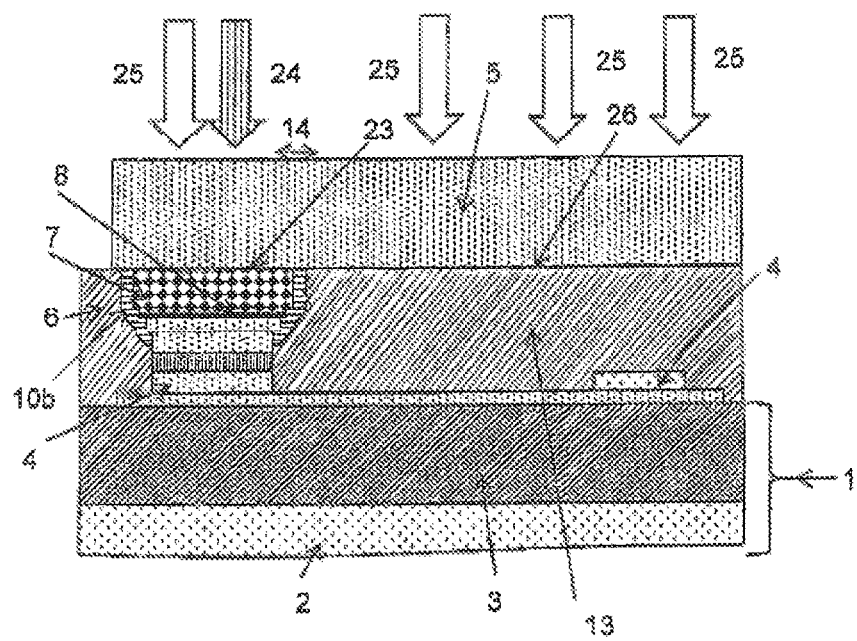
FIG. 2b shows a schematic illustration of the carrier substrate with attached working substrate after second polymer layer is drawn with reduced pressure into the region between the singulated LED structures.

After the aligned wafer bonding, in a method step D-0 the second polymer layer 13 is drawn with reduced pressure into the region 22 between the singulated LED structures, as shown in FIG. 2*b*. The singulated LED structures 6 are thereby stabilized by the second polymer layer 13, but the flexibility of the micro-LED matrix is maintained. As a result, the second flexible polymer layer 13 supports in particular an overhang 14 of the n-doped GaN layer 7 and the p-doped GaN layer 8 relative to the first contact-making structure 4 and the carrier substrate 1. FIG. 2*a* correspondingly shows the state before method step D-0. FIG. 2*b* correspondingly shows the state after step D-0.

In a method step D the laser lift-off process takes place in two substeps: firstly, the first application of laser radiation 24, shown in FIG. 2*b*, takes place only at interfaces 23 between the working substrate and the LED structures 6. In this case, the first application of laser radiation 24 takes place from the side of the working substrate 5 through the working substrate 5. In this first substep, the LED structures 6 are at least partly detached from the working substrate 5.

In a second substep in method step D, over the whole area the surface 26 of the LED structures 6 and of the second flexible polymer layer 13 which adjoins the working substrate 5 has a second laser radiation 25 applied to it, also indicated in FIG. 2*b*, and is thereby detached from the working substrate 5. The second application of laser radiation 25 over the whole area takes place with half the power of the first application 24. The working substrate 5 is removed after the second application of laser radiation 25.

In an additional method step E-0 before method step E, after the laser lift-off process, a second contact-making structure 15 for interconnecting the LED structures 6 is applied to the embedded LED structures 6. The second contact-making structure 15 is formed as a metallic contact-making structure by a lithographic method. This can be done by masking layers being patterned by lithography and being transferred to a previously applied metal layer by an etching process or with the aid of a lift-off process.

Figure 3:
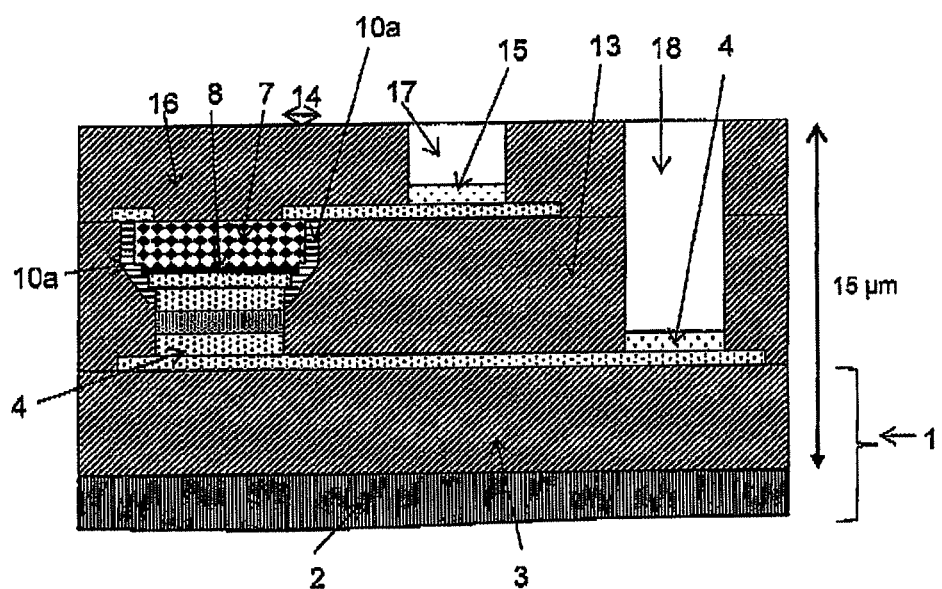

The second contact-making structure 15 can be seen in FIG. 3.

In a further method step E a third flexible polymer layer 16 is applied to the second flexible polymer layer 13, the second contact-making structure 15 and the embedded LED structures 6.

In a further method step, contact trenches 17 and 18 are formed, which enable contact to be made with the first and second contact-making structures 4 and 15 from above. This state is illustrated in FIG. 3. The contact trenches to the p-type and n-type contact-making structures are opened for example by dry etching using lithographically patterned resist masks. The geometry of the micro-LED matrix is defined during this processing step. Geometrically different components can be produced depending on the position of the contact trenches and thus the contact-making.

FIG. 3 thus illustrates an excerpt from a micro-LED matrix after an exemplary embodiment of the method according to the invention has been carried out. The micro-LED matrix in accordance with FIG. 3 constitutes an exemplary embodiment of a micro-LED matrix according to the invention:

The LED structure 6 is embedded into a flexible environment, comprising the first flexible polymer layer 3, the first contact-making structure 4, the second flexible polymer layer 13, the second contact-making structure 15 and the third flexible polymer layer 16. The first flexible polymer layer 3 is formed of a flexible biocompatible polymer, for example polyimide, and has a thickness of approximately 5 µm. The second flexible polymer layer 13 also consists of a flexible biocompatible polymer, for example epoxy resin or BCB (bisbenzocyclobutene), and has a thickness of approximately 5 µm. The second flexible polymer layer 13 supports the overhang 14 of the LED structure 6. The third flexible polymer layer 16 is formed of a flexible biocompatible polymer, for example polyimide, and serves for electrical insulation. The thickness of the third flexible polymer layer 16 is likewise approximately 5 µm.

The third flexible polymer layer 16 is perforated by a number of contact trenches 17 and 18. The contact trench 17 extends through the third flexible polymer layer 16 and thus enables the interconnection of the n-type contact 15. The contact trench 18 likewise extends through the second flexible polymer layer 13 in addition to the third flexible polymer layer 16 and thus enables the interconnection of the p-type contact 4.

Figure 4:
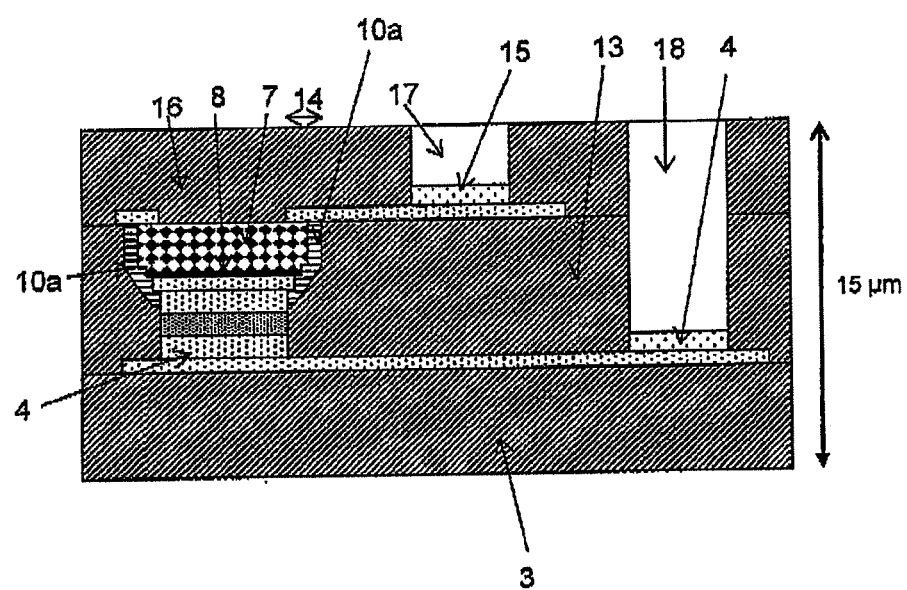

The micro-LED matrix can then be removed from the carrier layer 2 of the carrier substrate 1. The result is illustrated in FIG. 4:

FIG. 4 shows an excerpt of a schematic illustration of the exemplary embodiment after removal from the carrier layer 2 of the carrier substrate 1. The component comprises a first flexible polymer layer 3, a first contact-making structure 4, a p-doped GaN layer 8, an n-doped GaN layer 7, two passivation layers 10*a* and 10*b*, a second contact-making structure 15, a second flexible polymer layer 13 and a third flexible polymer layer 16. For interconnecting the LED structure, the contact-making trench 17 perforates the third flexible polymer layer as far as the second contact-making structure 15. The contact-making trench 18 perforates the third flexible polymer layer 16 and the second polymer layer 13 as far as the first contact-making structure 4. This enables the LED structure 6 to be interconnected on the front side and on the back side. Due to the interconnection on both sides, a substantially vertical current flow takes place in the LED structure 6. The dimensions of the LED structure in a vertical direction are 5 µm. In a horizontal direction, by contrast, the LED structures have significantly larger dimensions of between 10 and 100 µm. Advantageously, therefore, the vertical current flow through the small dimensions of the LED structure 6 in a vertical direction does not lead to a high series resistance.

During the use of the LED structure 6, the light emission takes place in particular toward the top in accordance with the illustration in FIG. 4.

Figure 5A:
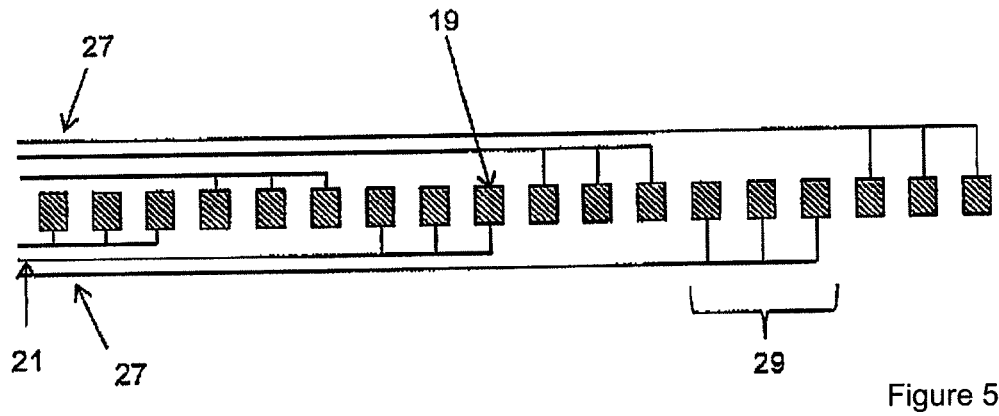
FIGS. 5a and 5b show schematic illustrations of contact-making schemes for the p-type and n-type contacts of the exemplary embodiment of a micro-LED matrix according to the invention.
Figure 5B:
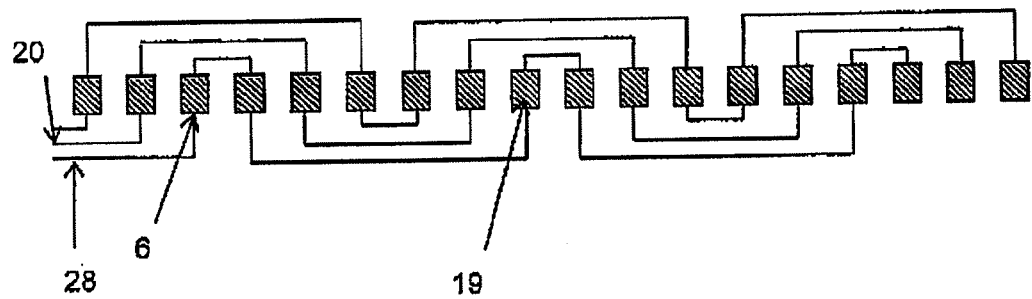

FIGS. 5*a* and 5*b* show two possible contact-making schemes for interconnecting the LED structures 6. The p-type contacts are interconnected according to the scheme illustrated in FIG. 5*a*. A total of six p-type leads 27 are present, which make contact with 18 LED structures 6 in such a way that each p-type lead 27 engages on the p-type contact of three LED structures 6 forming a p-type grouping 29. FIG. 5*b* illustrates the scheme for making contact with the n-type contacts. Here a total of three n-type leads 28 are present, which make contact with 18 LED structures 6 in such a way that each of the three n-type leads 28 makes contact exactly once with each p-type grouping 29 that arises as a result of the p-type leads 27 of the p-type contact-making.

In FIG. 5*a*, each of the six p-type leads 27 leads to a p-type grouping 29 comprising three LED structures 6. Contact is made with each of the LED structures 6 by the p-type lead at its p-type contact. Since the different LED structures 6 are insulated from one another, this results in six p-type groupings 29 each comprising three LED structures 6, with which groupings 29 contact is made in each case by an individual p-type lead 27.

In FIG. 5*b*, the three n-type leads 28 run in such a way that each n-type lead 28 makes contact—at the n-type contact—with a different LED structure 6 from each of the p-type groupings 29 that have been formed by the p-type contact-making. The three leads 28 therefore each made contact with six LED structures 6 from six different p-type groupings 29.

This type of contact-making enables a total of $k^2/2$ LED structures 6 to be driven individually with a number of k leads on the n-type and k/2 on the p-type contact side.

By way of example, a description is given hereinafter of how the LED structure 19 can be driven: in order to activate the LED structure 19, contact is made with the n-type contact via the central n-type lead 20, illustrated in FIG. 5*b*. Contact is made with the p-type contact via the lower central p-type lead 21, illustrated in FIG. 5*a*. Only the LED structure 19 is driven by the combination of the leads 20 and 21 since it is only for this LED structure 19 that contact is made both with the p-type contact and with the n-type contact.

The invention claimed is:

1. A method for producing a flexible micro-LED matrix comprising the following method steps:
    A depositing an LED layer structure onto a working substrate (5);
    B singulating a plurality of LED structures (6) from the LED layer structure on the working substrate (5) into singulated LED structures (6);
    C applying a first contact-making structure (4) to a carrier substrate (1);
    D bonding the working substrate (5) to the carrier substrate (1), filling a second flexible polymer layer (13) between the singulated LED structures (6) to form embedded LED structures, and transferring the embedded LED structures (6) from the working substrate (5) to the carrier substrate (1) by laser lift-off; and
    an at least two-layered carrier substrate (1) is used, comprising a carrier layer (2) and a first flexible polymer layer (3), in method step C the first contact-making structure (4) is applied indirectly or directly to that side of the first flexible polymer layer (3) which faces away from the carrier layer (2).

2. The method as claimed in claim 1, wherein
    in an additional method step E, a third flexible polymer layer (16) is applied to the second flexible polymer layer (13) and the embedded LED structures (6).

3. The method as claimed in claim 2, wherein
    in an additional method step E-0 before method step E a second contact-making structure (15) formed as a metallic contact-making structure, is applied at least to the embedded LED structures (6).

4. The method as claimed in claim 1, wherein
    the singulation of the plurality of LED structures (6) in method step B is effected by at least one of laser ablation or etching.

5. The method as claimed in claim 2, wherein
    a flexible biocompatible polymer is used for at least one of the first flexible polymer layer (3), the second flexible polymer layer (13), or the third flexible polymer layer (16).

6. The method as claimed in claim 1, wherein
    the second flexible polymer layer (13) is introduced into a region between the singulated LED structures (6) by application of reduced pressure.

7. The method as claimed in claim 1, wherein
    the carrier layer (2) of the at least two-layered carrier substrate (1) is removed by a peel-off process in a method step F.

* * * * *